United States Patent
Stenzel

(10) Patent No.: US 8,419,680 B2
(45) Date of Patent: Apr. 16, 2013

(54) RAPID EXCHANGE PRE-DILATOR

(75) Inventor: Eric B. Stenzel, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1532 days.

(21) Appl. No.: 11/166,539

(22) Filed: Jun. 24, 2005

(65) Prior Publication Data

US 2007/0010863 A1 Jan. 11, 2007

(51) Int. Cl.
*A61M 29/00* (2006.01)
*A61F 2/06* (2006.01)

(52) U.S. Cl.
USPC ........ 604/103.04; 604/104; 606/191; 623/1.1

(58) Field of Classification Search ............. 604/103.04, 604/104, 264; 623/1.1; 606/191
See application file for complete search history.

(56) References Cited

U.S. PATENT DOCUMENTS

| | | | |
|---|---|---|---|
| 1,888,349 A | 11/1932 | Jacoby | |
| 5,308,354 A | 5/1994 | Zacca et al. | 606/159 |
| 5,320,610 A * | 6/1994 | Yoon | 604/158 |
| 5,357,978 A | 10/1994 | Turk | 128/772 |
| 5,409,470 A | 4/1995 | McIntyre et al. | 604/283 |
| 5,448,993 A | 9/1995 | Lynch et al. | 128/657 |
| 5,871,475 A | 2/1999 | Frassica | 604/624 |
| 5,921,982 A * | 7/1999 | Lesh et al. | 606/41 |
| 5,957,903 A | 9/1999 | Mirzaee et al. | 604/282 |
| 6,322,586 B1 | 11/2001 | Monroe et al. | |
| 6,517,518 B2 * | 2/2003 | Nash et al. | 604/164.02 |
| 2002/0052641 A1 | 5/2002 | Monroe et al. | |
| 2003/0208153 A1 | 11/2003 | Stenzel | 604/60 |
| 2005/0075647 A1 | 4/2005 | Walters et al. | 606/108 |

FOREIGN PATENT DOCUMENTS

| | | |
|---|---|---|
| EP | 1374943 | 1/2004 |
| WO | 03/004084 | 1/2003 |
| WO | 03084592 | 10/2003 |

* cited by examiner

*Primary Examiner* — Victoria P Shumate
(74) *Attorney, Agent, or Firm* — Seager, Tufte & Wickhem, LLC

(57) ABSTRACT

A predilation device may comprise a shaft portion and a distal tip having helical threadings. The predilation device may further include a rapid exchange element rotatably coupled to the shaft portion. A guidewire may slidably engage the rapid exchange element and may guide the predilation device to a lesion site. The predilation device may be positioned with the distal tip abutting the lesion. The shaft portion may be rotated, thereby rotating the tip and causing the tip to pass through the lesion and predilate the lesion. In some embodiments, the tip may remove lesion material.

23 Claims, 5 Drawing Sheets

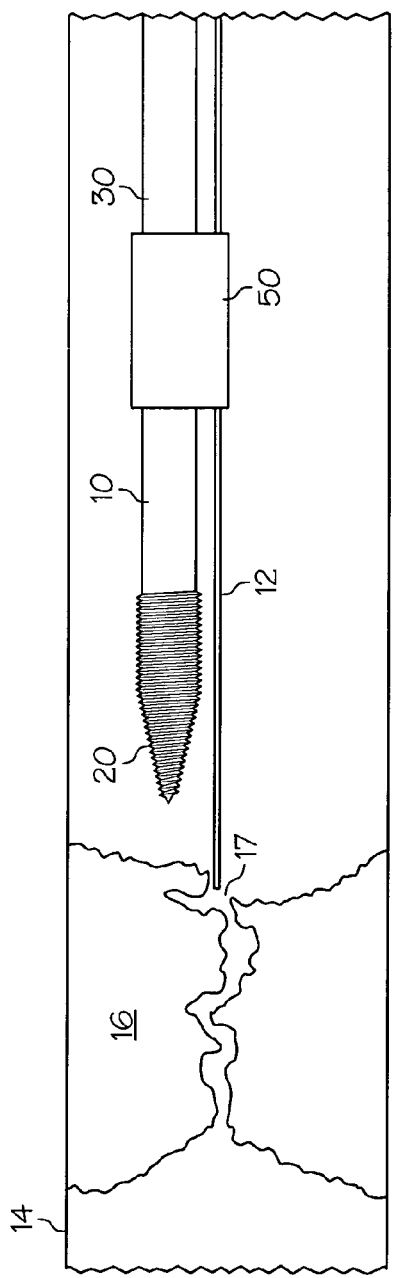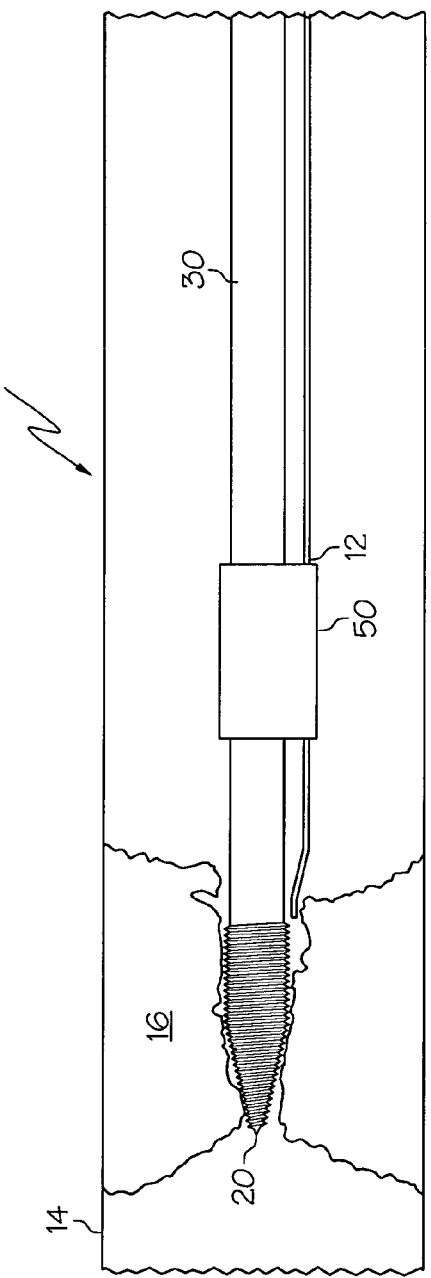

# RAPID EXCHANGE PRE-DILATOR

BACKGROUND OF THE INVENTION

Angioplasty catheters, stents and stent delivery systems are generally known in the art. Both over-the-wire and rapid-exchange type catheters are known. An inflation balloon may be delivered to a deployment site, such as a lesion or occlusion, in a reduced or unexpanded configuration. Once properly positioned within a lesion, the balloon may be expanded, thereby dilating the lesion. In some cases, a stent may be delivered to the site of a lesion where it may be used, sometimes in conjunction with an inflation balloon, to dilate the lesion and/or to support a vessel at the site of a dilated lesion.

When vessels are significantly occluded, it may be difficult to position an inflation balloon or unexpanded stent across the lesion. It may even be difficult to cross the lesion with a guidewire. The options generally available for treating a significantly or completely occluded vessel include using a rotational atherectomy device to debulk hard and/or calcified lesion material, or invasive bypass surgery.

There remains a need for a device capable of predilating a lesion. A predilation may allow for an inflation balloon and/or stent delivery system to traverse the lesion, thereby providing an alternative to rotational atherectomy devices or invasive bypass surgery.

Desirably, a predilation device may be capable of rapid-exchange type operation.

Further, there remains a need for a device capable of allowing an over-the-wire type catheter to be used in a rapid-exchange type method.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, a predilation device may comprise a catheter shaft having a distal tip, the distal tip having helical threadings, and a rapid exchange element having a first internal passageway and a second internal passageway. A portion of the catheter shaft may pass through the first internal passageway, and the rapid exchange element may be rotatably coupled to the shaft. The rapid exchange element may further be fixed against moving along the axis of the shaft.

A predilation device may further comprise a guidewire adjacent to the catheter shaft, and a portion of the guidewire may pass through the second internal passageway of the rapid exchange element.

In some embodiments, a predilation device may further comprise a stent oriented about the shaft between the tip and the rapid exchange element. In some embodiments, a predilation device may further comprise an inflation balloon oriented about the shaft between the tip and the rapid exchange element. In some embodiments a stent may be oriented about an inflation balloon. An outer diameter of the tip may be equal to or greater than an outer diameter of the stent and/or balloon when the stent/balloon is unexpanded.

In another embodiment, a predilation device may comprise a shaft having a distal tip and an inner lumen, the inner lumen extending through the tip. The distal tip may be made of metal and may have helical threadings.

In some embodiments, a method of predilating a lesion may comprise positioning a guidewire within a vessel such that a distal end of the guidewire reaches a lesion. A predilation device as described herein may be guided to the lesion using the guidewire. The predilation device may be positioned with the tip abutting the lesion. The catheter shaft may be rotated and advanced thereby causing the tip to remove lesion material and predilate the lesion. The predilation device may be removed and a stent may be placed across the predilated lesion.

In some embodiments, the invention is also directed to a rapid exchange clip having a catheter lumen extending therethrough and a guidewire lumen extending therethrough. The rapid exchange clip may be clipped onto a catheter shaft and may engage the catheter shaft. In some embodiments, the rapid exchange clip may frictionally engage a catheter. The use of a rapid exchange clip may allow a non-rapid exchange type catheter to function or be used as a rapid exchange catheter.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

FIG. 12 shows an embodiment of a predilation device within a vessel approaching a lesion site.
FIG. 13 shows an embodiment of a predilation device in the process of predilating a lesion.

DETAILED DESCRIPTION OF THE INVENTION

Figure 1:
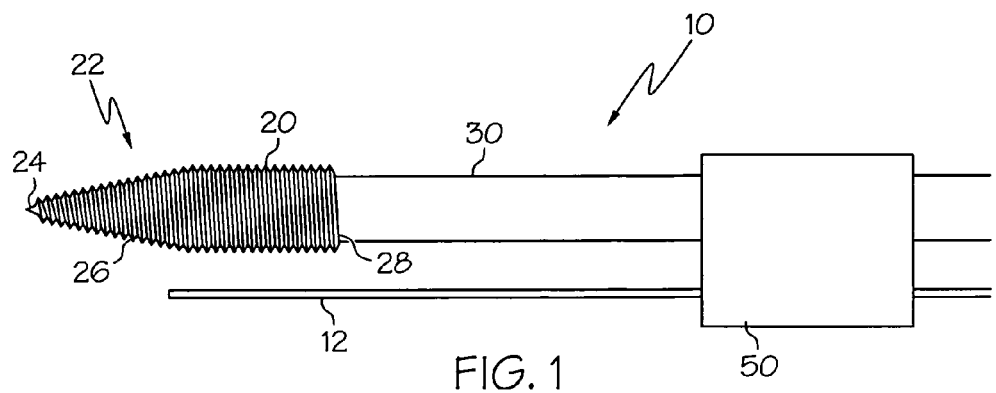
FIG. 1 shows an embodiment of a predilation device.

While this invention may be embodied in many different forms, there are described in detail herein specific preferred embodiments of the invention. This description is an exemplification of the principles of the invention and is not intended to limit the invention to the particular embodiments illustrated.

U.S. Pat. Nos. 6,746,475; 6,733,524; 6,730,117; 6,695,877; 5,871,475; 6,866,660; 6,786,887; and 6,767,338 are hereby incorporated herein by reference in their entireties.

For the purposes of this disclosure, like reference numerals in the figures shall refer to like features unless otherwise indicated.

FIG. 1 shows an embodiment of a predilation device 10 which may be used to predilate a lesion, occlusion, or other obstruction within a vessel. The predilation device 10 may generally comprise a shaft portion 30 and a distal tip 20. In some embodiments, the shaft portion 30 may have a substantially constant diameter along its length. The shaft portion 30 may extend proximally and may be of any suitable length to extend outside of a patient's body. Desirably, the proximal end of the shaft portion 30 may be rotated, which may cause rotation of the entire shaft portion 30 and tip 20. The shaft portion 30 may be made of any suitable material, such as catheter materials including, but not limited to, moldable polymers, polyether block amide (PEBA), nylon or polyethyleneterephthalate (PET), polyurethane, latex, silicone rubber, natural rubber, polyvinyl chloride, polyamide, polyamide elastomer, copolymer of ethylene and vinyl acetate, polyethylene, polyimide, stainless steel and suitable alloy materials such as nickel-titanium alloys, cobalt-chromium-nickel alloys, etc.

The distal tip 20 is desirably coupled to and arranged to rotate with the shaft portion 30. The tip 20 desirably includes a tapered portion 22 which may taper to a point 24, or in some embodiments may taper to a blunted or rounded point. The tip 20 desirably includes a shaped surface which allows for grinding, screwing or burrowing into a lesion or occlusion. For example, the tip 20 may include threadings 26 which may spiral in helical fashion from the distal point 24 to a proximal end 28 of the tip 20. Desirably the threadings 26 may be arranged to allow the predilation device 10 to burrow into an occlusion as the shaft portion 30 is rotated, for example in a clockwise direction.

The tip 20 may be made from any suitable materials, such as polymers, ceramics and metals including implant grade stainless steel such as 316LS. A tip may be formed using any suitable method including molding, casting, machining, grinding, laser ablation, etc. In some embodiments the tip 20 may comprise the same material as the shaft 30. In some embodiments, the shaft 30 may be molded, extruded and machined or otherwise manufactured with an integral tip 20. In some embodiments, the tip 20 may comprise a separate piece and may be attached to the shaft 30 using any suitable method, such as crimping, swaging, gluing, welding, fusing, etc., as well as any type of mechanical cooperation between the tip 20 and the shaft 30, such as screw threadings, click-fit connections, press-fit connections, etc.

In some embodiments, the largest outer diameter of the threadings 26 may be greater than the outer diameter of the shaft 30.

The predilation device 10 may further comprise a rapid exchange clip 50 which may be rotatably attached to the shaft portion 30 and may provide for sliding engagement with a guidewire 12.

Figure 2:
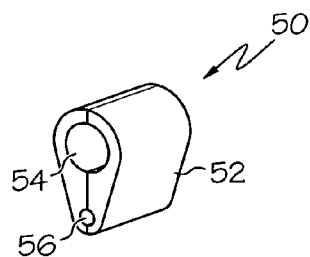
FIG. 2 shows an embodiment of a rapid exchange clip.
Figure 3:
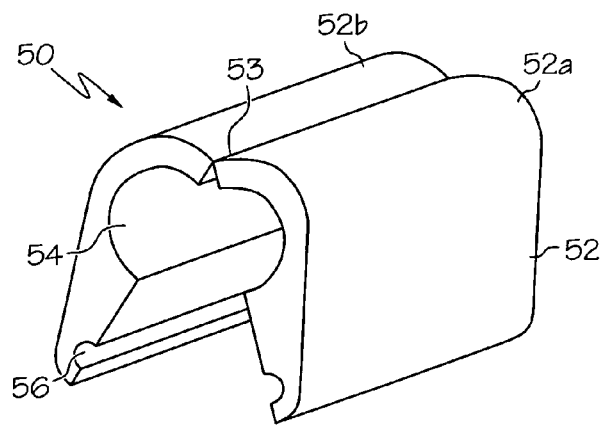
FIG. 3 shows another view of the rapid exchange clip of FIG. 2.

FIGS. 2 and 3 show an embodiment of a rapid exchange clip 50 in greater detail. A rapid exchange clip 50 may include a body portion 52 having a first passageway 54 and a second passageway 56 extending therethrough. The first passageway 54 may be larger than the second passageway 56, for example having a larger diameter. The first passageway 54 may run parallel to the second passageway 56. A rapid exchange clip 50 may be made from any suitable material such as metals, ceramics, moldable polymers, etc.

A rapid exchange clip 50 may include a first body portion 52a and a second body portion 52b, which may be connected together. For example, the two body portions 52a, 52b may be connected via a hinge connection 53. The two body portions 52a, 52b may further include a suitable engagement mechanism (not shown) to hold the rapid exchange clip 50 closed when it is positioned about the shaft portion 30 of the predilation device 10. For example, one body portion 52a may include protruding pins that are constructed and arranged to engage complimentary apertures or holes in the other body portion 52b. In other embodiments, the body portions 52a, 52b could include snap tabs, complimentary ties, a hook and latch, or any other suitable engagement mechanism.

When a rapid exchange clip 50 is properly positioned and installed with respect to the shaft 30, the shaft 30 may extend through the first passageway 54. Desirably, the shaft 30 is free to rotate within the first passageway 54. In some embodiments, the rapid exchange clip 50 may engage the shaft 30 such that, although the shaft 30 remains free to rotate, the rapid exchange clip 50 is fixed against moving axially along the length of the shaft 30.

A guidewire 12 may be positioned within the second passageway 56. Desirably the second passageway 56 and guidewire 12 are dimensioned such that the guidewire 12 may move freely with respect to the rapid exchange clip 50, and the rapid exchange clip 50 may slide along the guidewire 12. Thus, a guidewire 12 may be used to guide the predilation device 10 to a lesion site.

A rapid exchange clip 50 may be provided as an integral portion of the predilation device or as a separate unit as depicted in FIGS. 2 and 3. When the rapid exchange clip 50 is a separate unit, the shaft 30 may be positioned next to a guidewire 12 and the rapid exchange clip 50 may be closed around the shaft 30 and the guidewire 12.

In some embodiments, rapid exchange clip 50 may be used to convert an over-the-wire type catheter or any non-rapid-exchange type catheter into a rapid-exchange type catheter. A rapid exchange clip 50 may be secured about any catheter, thereby giving the catheter the capability of rapid-exchange functionality via the second passageway/guidewire lumen 56 of the rapid exchange clip 50. In some embodiments, the rapid exchange clip 50 material defining the first passageway/catheter lumen 54 may frictionally engage a catheter. In some embodiments, the first passageway 54 may include an internal raised flange which may contact and engage a catheter. Any embodiment of a rapid exchange clip 50 described herein may be used with a prior art catheter to provide rapid exchange functionality. Thus, in some embodiments, a rapid exchange clip 50 may be rotationally engaged with a non-rapid-exchange type catheter shaft.

Various embodiments of a predilation device 10 may be provided with various amounts of shaft 30 length between the tip 20 and the rapid exchange clip 50.

Figure 4:
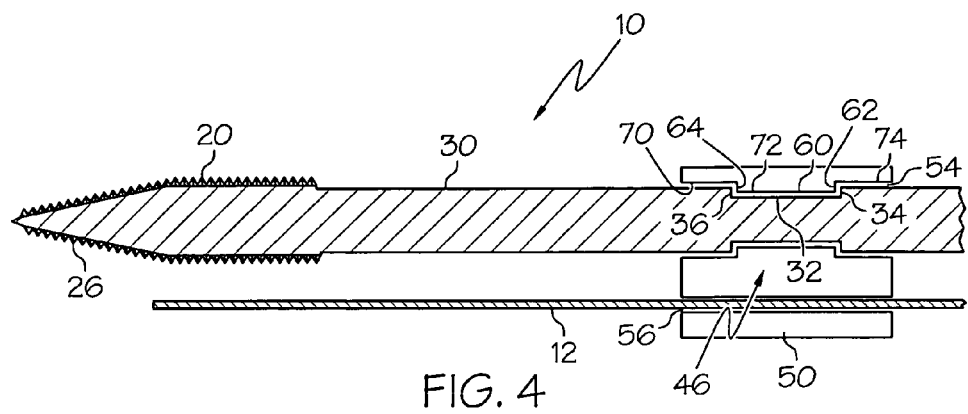
FIG. 4 shows a sectional view of another embodiment of a predilation device.

FIG. 4 shows an embodiment of a predilation device 10 having an engagement mechanism 46 between the shaft 30 and the rapid exchange clip 50 which allows the shaft 30 to rotate yet remain axially fixed with respect to the rapid exchange clip 50. The first passageway 54 of the rapid exchange clip 50 may include a raised flange 60 which may be annular in shape. The raised flange 60 may be made from a separate material or from the same material as the rapid exchange clip 50. Desirably, the raised flange 60 may be formed integrally with the rapid exchange clip 50, for example during molding of the rapid exchange clip 50.

The raised flange 60 may include a proximal lateral surface 62 and a distal lateral surface 64. The portion of the first passageway 54 having the raised flange 60 desirably has an inner diameter that is less than the inner diameter of other portions of the first passageway 54. The first passageway 54 may also be described as having a first portion 70, second portion 72 and third portion 74, wherein the internal diameter of the second portion 72 is less than the internal diameter of the first portion 70. The internal diameter of the second portion 72 may also be less than the internal diameter of the third portion 74. The internal diameter of the first portion 70 may be approximately equal to the internal diameter of the third portion 74.

The shaft 30 may include an annular groove 32 that is arranged to engage the raised flange 60 of the rapid exchange clip 50. The groove 32 may include a proximal lateral wall 34 and a distal lateral wall 36. When the rapid exchange clip 50 is positioned about the shaft 30, desirably the raised flange 60 of the rapid exchange clip 50 sits within the groove 32 of the shaft 30. The distal lateral wall 36 of the shaft 30 may abut the distal lateral surface 64 of the raised flange 60 and may prevent the shaft 30 from moving proximally with respect to the rapid exchange clip 50. The proximal lateral wall 34 of the shaft 30 may abut the proximal lateral surface 62 of the raised flange 60 and prevent the shaft 30 from moving distally with respect to the rapid exchange clip 50. Thus, the interaction between the raised flange 60 and the groove 32 allows the shaft 30 to rotate with respect to the rapid exchange clip 50 while fixing the position of the rapid exchange clip 50 along the length of the shaft 30.

Figure 5:
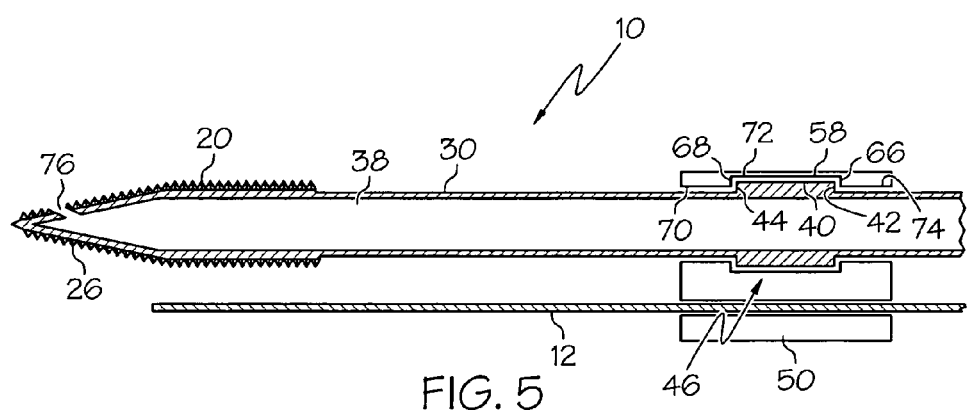
FIG. 5 shows a sectional view of another embodiment of a predilation device.

FIG. 5 shows another embodiment of a predilation device 10 having another embodiment of an engagement mechanism 46 between the shaft 30 and the rapid exchange clip 50 which allows the shaft 30 to rotate yet remain axially fixed with respect to the rapid exchange clip 50. The first passageway 54 of the rapid exchange clip 50 may include a groove 58 which may be annular in shape. The groove 58 may include a proximal lateral wall 66 and a distal lateral wall 68. The portion of the first passageway 54 having the groove 58 desirably has an inner diameter that is greater than the inner diameter of other portions of the first passageway 54. The first passageway 54 may also be described as having a first portion 70, second portion 72 and third portion 74, wherein the internal diameter of the second portion 72 is greater than the internal diameter of the first portion 70. The internal diameter of the second portion 72 may also be greater than the internal diameter of the third portion 74. The internal diameter of the first portion 70 may be approximately equal to the internal diameter of the third portion 74.

The shaft 30 may include a raised flange 40 which may be annular in shape and may be arranged to engage the groove 58 of the rapid exchange clip 50. The raised flange 40 may include a proximal lateral surface 42 and a distal lateral surface 44. When the rapid exchange clip 50 is positioned about the shaft 30, desirably the raised flange 40 of the shaft 30 sits within the groove 58 of the rapid exchange clip 50. The distal lateral wall 68 of the groove 58 may abut the distal lateral surface 44 of the raised flange 40 and may prevent the shaft 30 from moving proximally with respect to the rapid exchange clip 50. The proximal lateral wall 66 of the groove 58 may abut the proximal lateral surface 42 of the raised flange 40 and prevent the shaft 30 from moving distally with respect to the rapid exchange clip 50. Thus, the interaction between the raised flange 40 and the groove 58 allows the shaft 30 to rotate with respect to the rapid exchange clip 50 while fixing the position of the rapid exchange clip 50 along the length of the shaft 30.

A raised flange 40 may be made from the same material as the shaft 30 or may be made from a different material. A raised flange 40 may comprise a section of larger diameter formed during the manufacturing process, such as during extrusion of the shaft 30. In some embodiments, a raised flange 40 may comprise a separate length of material which is coupled to and positioned between a distal length and proximal length of the shaft 30. In some embodiments, a raised flange 40 may comprise a ring or collar that is positioned about the shaft 30.

Figure 6:
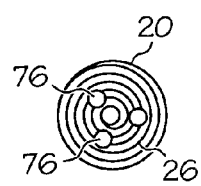
FIG. 6 shows an end view of another embodiment of a tip.

FIGS. 5 and 6 show an embodiment of a predilation device 10 wherein the shaft 30 and tip 20 may include an internal cavity 38 or fluid passageway. The tip 20 may include one or more apertures 76 which may be in fluid communication with the internal cavity 38. Plaque or other lesion material being removed by the predilation device 10 may be drawn through the apertures 76, through the internal cavity 38 along the length of the shaft 30 and may be exhausted out the proximal end of the shaft 30. In some embodiments, suction may be applied to the proximal end of the shaft 30 to actively draw lesion material into the internal cavity 38 and carry it away.

Figure 7:
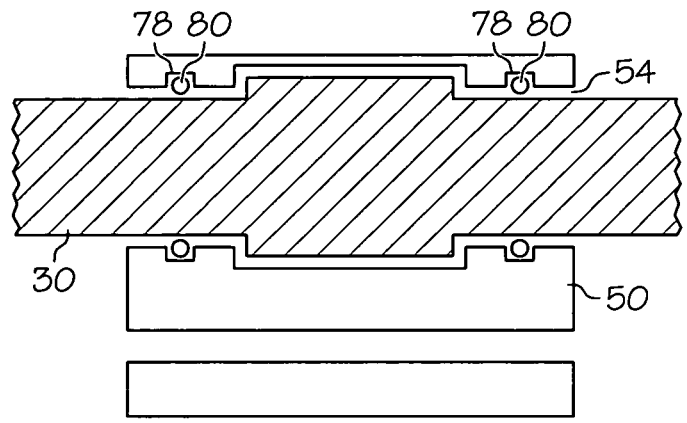
FIG. 7 shows another embodiment of a rapid exchange clip.
Figure 8:
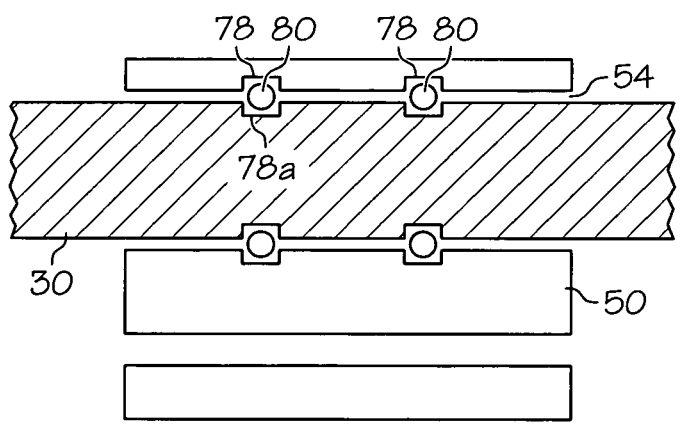
FIG. 8 shows a further embodiment of a rapid exchange clip.

FIGS. 7 and 8 show portions of further embodiments of a predilation device 10. A rapid exchange clip 50 may further include one or more bearing grooves 78, which may be annular in shape. The inner diameter of a bearing groove 78 is desirably larger than the inner diameter of the first passageway 54 immediately adjacent to the bearing groove 78. A plurality of ball bearings 80 may be positioned within each bearing groove 78. The ball bearings 80 may abut the inner surface of the bearing groove 78 and may abut a surface of the shaft 30, thereby allowing the shaft 30 to rotate smoothly within the first passageway 54 of the rapid exchange clip 50. In another embodiment (not shown), a bearing groove 78 may be located in the shaft 30 as opposed to the rapid exchange clip 50.

FIG. 8 shows an embodiment where the rapid exchange clip 50 may include a bearing groove 78 and the shaft 30 may include a complimentary bearing groove 78a. Ball bearings 80 may sit partially within the bearing groove 78 and partially within the complimentary bearing groove 78a. In embodiments having this feature, the interaction of the bearing grooves 78, 78a and the ball bearings 80 may prevent the rapid exchange clip 50 from displacing along the axis of the shaft 30.

Figure 9:
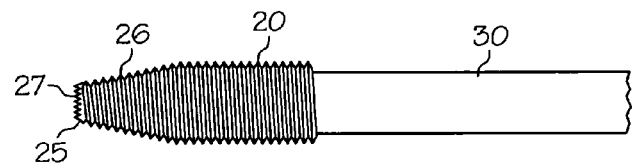
FIG. 9 shows another embodiment of a tip.

FIG. 9 shows another embodiment of a tip 20, which may include threadings 26. The distal end of the tip 20 may further include a grinding portion 25, which may include teeth 27, ridges or any other suitable textured surface which may be used to grind into a lesion. In some embodiments, the teeth 27 or portions of a textured surface may be rigid and/or sharp. A tip 20 which includes a grinding portion 25 may be useful for grinding into partially or totally occluded or calcified lesions.

Figure 10:
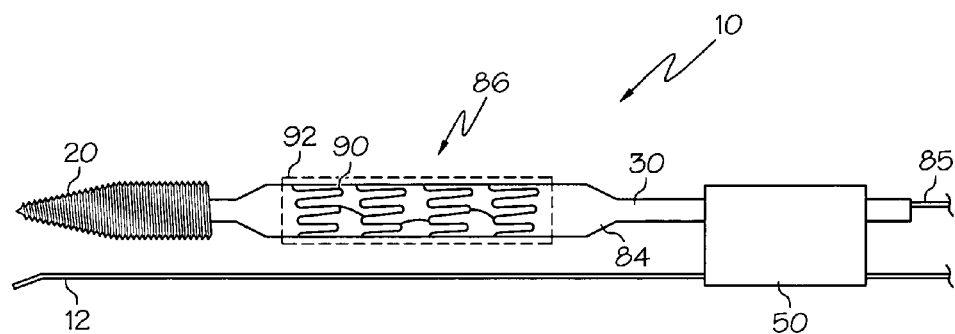
FIG. 10 shows another embodiment of a predilation device.

FIG. 10 shows another embodiment of a predilation device 10, which may include a shaft 30, tip 20 and rapid exchange clip 50 as herein described. The predilation device 10 may further comprise an inflation balloon 84 and/or a stent delivery section 86, which may be located between the tip 20 and the rapid exchange clip 50. In some embodiments, a stent delivery section 86 may include an inflation balloon 84. A stent delivery section 86 may further include a stent 90 or other expandable medical device, which may include balloon expandable stents, self-expanding stents, and the like. A balloon expandable stent may be positioned over a folded inflation balloon 84 in an unexpanded state. A self-expanding stent may be positioned directly over the shaft 30, or in some embodiments over a folded inflation balloon 84 in an unexpanded state. A self-expanding stent may further be covered by a retractable sheath 92 which may retain the stent 90 in an unexpanded state.

When a predilation device 10 includes an inflation balloon 84, the shaft 30 desirably includes an inflation lumen 85 which may be in fluid communication with an interior portion of the inflation balloon 84. In some embodiments, a shaft 30 may comprise an inner shaft and an outer shaft. The inner shaft may be coupled to a distal end of the inflation balloon 84, and the outer shaft may be coupled to the proximal end of the inflation balloon 84. The area between the inner and outer shafts may comprise an inflation lumen.

An inflation balloon 84 and/or stent delivery section 86 may be initially provided in an unexpanded configuration having an unexpanded outer diameter. In some embodiments, the outer diameter of the tip 20 may be equal to or greater than the unexpanded outer diameter of the inflation balloon 84 and/or stent delivery section 86. This allows the inflation balloon 84 and/or stent delivery section 86 to be positioned within a lesion that has been predilated using the predilation device 10.

Figure 11:
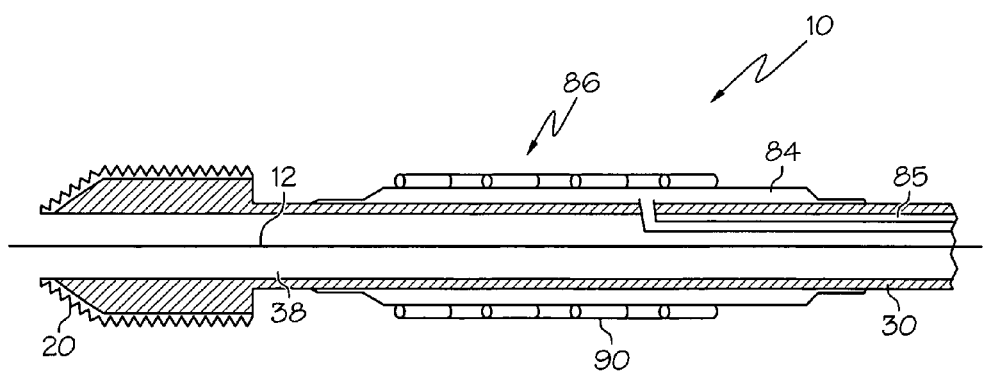
FIG. 11 shows a sectional view of another embodiment of a predilation device.

FIG. 11 shows a sectional view of another embodiment of a predilation device 10 which may comprise an over-the-wire device. The predilation device 10 may include a tip 20 and shaft 30, each having an inner cavity 38 or lumen extending therethrough. A guidewire 12 may extend through the inner cavity 38 or lumen. Thus, a predilation device 10 may be placed over a guidewire 12 and may follow the guidewire 12 to a lesion site.

The predilation device 10 may further include an inflation balloon and/or stent delivery system as discussed with respect to FIG. 10. Desirably, the outer diameter of the tip 20 may be equal to or greater than the outer diameter of the unexpanded inflation balloon and/or stent delivery system.

In some embodiments, a predilation device 10 may include a piercing jaw as disclosed in Published US Patent Application No. 2003/0208153, the entire disclosure of which is incorporated herein by reference in its entirety.

An example method of using a predilation device 10 will be discussed with reference to FIGS. 12 and 13. FIG. 12 shows a vessel 14 having a lesion 16. Generally, a guidewire 12 may be maneuvered through the body to the site of the lesion 16. In some cases, the size and shape of the lesion 16 may block the vessel 14 to the extent that the guidewire 12 is unable to cross the lesion 16. It may be desirable to predilate the lesion 16 in order to allow a guidewire 12, angioplasty balloon or stent delivery system to be positioned within the lesion 16.

A predilation device 10 may be delivered to the lesion 16 site. The rapid exchange clip 50 may be used to slidably engage the guidewire 12, thereby allowing the predilation device 10 to follow the guidewire 12 to the lesion 16 site. The predilation device 10 may be positioned with its tip 20 abutting the lesion 16. If a lumen 17 or partial lumen exists through at least a portion of the lesion 16, the tip 20 may be positioned as far into the existing lumen 17 as possible.

A proximal end of the shaft 30 of the predilation device 10 may be rotated from outside the patient's body. The entire length of the shaft 30 may rotate, thereby causing rotation of the tip 20. The rotatable engagement between the shaft 30 and the rapid exchange clip 50 desirably allows the shaft 30 to rotate without disturbing placement of the rapid exchange clip 50 or the guidewire 12. As the tip 20 rotates, it may remove lesion 16 material and burrow or screw through the lesion 16, thereby predilating the lesion as depicted in FIG. 13.

Once a lesion 16 has been predilated, the predilation device 10 may be retracted and removed from the vessel 14. The guidewire 12 may be repositioned and extended through the predilated lesion 16. A stent delivery system may then follow the guidewire 12 to the lesion 16, and a stent may be placed across the predilated lesion. Thus, a predilation device 10 allows a significantly or totally occluded lesion to be crossed and stented.

In embodiments where a predilation device 10 includes an inflation balloon or stent delivery section, for example as disclosed with respect to FIGS. 10 and 11, once the lesion 16 has been predilated, the inflation balloon or stent delivery section may immediately be positioned within the predilated lesion.

In some embodiments, the invention is directed to a rapid exchange clip and methods of using a rapid exchange clip, for example as described in the following paragraphs.

1. A rapid exchange clip comprising:
a first body portion and a second body portion constructed and arranged to engage a catheter, the first body portion and a second body portion cooperatively defining a catheter passageway and a guidewire passageway, wherein the rapid exchange clip may be oriented about a catheter shaft, and the catheter passageway frictionally engages the catheter shaft.

2. The rapid exchange clip of paragraph 1, wherein a guidewire may be oriented adjacent to said catheter shaft; a portion of the guidewire passing through the guidewire passageway.

3. The rapid exchange clip of paragraph 1, wherein the rapid exchange clip is fixed against moving along the length of the catheter shaft.

4. The rapid exchange clip of paragraph 3, wherein the catheter passageway includes a raised flange which frictionally engages the catheter shaft.

5. The rapid exchange clip of paragraph 3, where in the catheter passageway includes a shaped wall portion constructed and arranged to rotatably engage the catheter shaft.

6. The rapid exchange clip of paragraph 1, wherein the first body portion and the second body portion are connected via a hinge.

7. The rapid exchange clip of paragraph 1, wherein the rapid exchange clip comprises a removable clip.

8. A method of using a catheter comprising:
providing a non-rapid-exchange type catheter shaft;
providing a guidewire;
providing a rapid exchange clip having a catheter passageway and a guidewire passageway;
securing the rapid exchange clip to the catheter shaft; and
orienting the guidewire within the guidewire passageway of the rapid exchange clip.

9. The method of paragraph 8, wherein the catheter passageway frictionally engages the catheter shaft.

10. The method of paragraph 8, wherein the rapid exchange clip is slidably engaged with the guidewire.

11. The method of claim 8, further comprising positioning the guidewire within a patient's body and using the guidewire to guide the rapid exchange clip and catheter shaft along a length of the guidewire.

In some embodiments, the invention is directed to methods of predilating a lesion using a predilation device 10, for example as described in the following numbered paragraphs.

1. A method of predilating a lesion comprising:
positioning a guidewire within a vessel, a distal end of the guidewire reaching a lesion;
providing a predilation device comprising:
a catheter shaft having a distal tip, the distal tip having helical threadings; and a rapid exchange element rotatably coupled to the catheter shaft, the rapid exchange element having a passageway therethrough;

positioning a portion of the guidewire within the passageway of the rapid exchange element and guiding the predilation device to the lesion using the guidewire;

positioning the predilation device with the tip abutting the lesion;

rotating the catheter shaft while advancing the catheter shaft, thereby causing the tip to pass through the lesion.

2. The method of paragraph 1, wherein the tip predilates the lesion as it passes through the lesion.

3. The method of paragraph 1, wherein the tip removes lesion material as it passes through the lesion.

4. The method of paragraph 3, wherein predilation device further includes an internal lumen extending therethrough; the tip further comprises an aperture in fluid communication with the internal lumen; wherein material removed from the lesion is drawn through the aperture and through the internal lumen to a proximal portion of the catheter shaft.

5. The method of paragraph 1, further comprising removing the predilation device and repositioning the guidewire across the predilated lesion.

6. The method of paragraph 5, further comprising using the guidewire to guide a stent delivery system to the lesion and positioning a stent across the predilated lesion.

7. The method of paragraph 6, further comprising dilating the lesion and expanding the stent.

8. A method of predilating a lesion comprising:

positioning a guidewire within a vessel, a distal end of the guidewire reaching a lesion;

providing a predilation and stent delivery device comprising:

a catheter shaft having a distal tip, the distal tip having helical threadings; a rapid exchange element rotatably coupled to the catheter shaft, the rapid exchange element having a passageway therethrough; and a stent oriented about the catheter shaft proximal to the distal tip;

positioning a portion of the guidewire within the passageway of the rapid exchange element and guiding the predilation and stent delivery device to the lesion using the guidewire;

positioning the predilation and stent delivery device with the tip abutting the lesion;

rotating the catheter shaft while advancing the catheter shaft, thereby causing the tip to pass through the lesion;

advancing the catheter shaft until the stent is positioned across the lesion; and expanding the stent.

9. The method of paragraph 8, wherein the tip predilates the lesion as it passes through the lesion.

10. The method of paragraph 8, wherein the tip removes lesion material as it passes through the lesion.

11. A method of predilating a lesion comprising:

positioning a guidewire within a vessel, a distal end of the guidewire reaching a lesion;

providing a predilation device comprising:

a catheter shaft having a distal tip and an inner lumen, the inner lumen extending through the tip, the distal tip having helical threadings;

positioning a portion of the guidewire within the inner lumen of the guidewire and guiding the predilation device to the lesion using the guidewire;

positioning the predilation device with the tip abutting the lesion;

rotating the catheter shaft while advancing the catheter shaft, thereby causing the tip to pass through the lesion.

12. The method of paragraph 11, wherein the tip predilates the lesion as it passes through the lesion.

13. The method of paragraph 11, wherein the tip removes lesion material as it passes through the lesion.

14. The method of paragraph 11, further comprising removing the predilation device and repositioning the guidewire across the predilated lesion.

15. The method of paragraph 14, further comprising using the guidewire to guide a stent delivery system to the lesion and positioning a stent across the predilated lesion.

16. The method of paragraph 15, further comprising dilating the lesion and expanding the stent.

17. The method of paragraph 11, wherein the tip further comprises an aperture in fluid communication with the internal lumen; wherein material removed from the lesion is drawn through the aperture and through the internal lumen to a proximal portion of the catheter shaft.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A predilator comprising:
   a catheter, the catheter comprising a catheter shaft defining a central axis, the shaft having a distal tip, the distal tip having helical threadings; and
   a rapid exchange element having a first internal passageway and a second internal passageway, a portion of the catheter shaft passing through the first internal passageway; wherein the rapid exchange element is rotatably coupled to the shaft allowing rotation of the shaft about its central axis when the rapid exchange element and at least a portion of the shaft are oriented within a body vessel.

2. The predilator of claim 1, further comprising a guidewire adjacent to said catheter shaft; a portion of the guidewire passing through the second internal passageway of the rapid exchange element.

3. The predilator of claim 1, wherein the rapid exchange element is fixed against moving along the axis of the shaft.

4. The predilator of claim 3, wherein the first internal passageway includes a raised flange which engages an annular groove in the catheter shaft.

5. The predilator of claim 3, wherein the catheter shaft includes a raised flange which engages an annular groove in the first internal passageway.

6. The predilator of claim 3, where in the first internal passageway includes a shaped wall portion constructed and arranged to rotatably engage the catheter shaft.

7. The predilator of claim 1, wherein the rapid exchange element comprises a removable clip.

8. The predilator of claim 1, wherein the rapid exchange element further comprises a bearing groove, and ball bearings within the bearing groove are arranged to roll between the bearing groove and the shaft.

9. The predilator of claim 1, wherein the shaft further comprises a bearing groove, and ball bearings within the bearing groove are arranged to roll between the bearing groove and the rapid exchange element.

10. The predilator of claim 1, wherein the shaft and distal tip further comprise an internal lumen, and the tip further includes an aperture in fluid communication with the internal lumen, the predilator configured to draw removed lesion material through said aperture and said internal lumen.

11. The predilator of claim 10, wherein the aperture is offset from the central axis of the shaft.

12. The predilator of claim 1, wherein the tip includes a distal grinding portion.

13. The predilator of claim 1, further comprising a stent oriented about the shaft between the tip and the rapid exchange element.

14. The predilator of claim 13, wherein an outer diameter of the tip is equal to or greater than an outer diameter of the stent when the stent is unexpanded.

15. The predilator of claim 1, further comprising an inflation balloon located between the tip and the rapid exchange element.

16. The predilator of claim 15, further comprising a stent oriented about the inflation balloon.

17. The predilator of claim 1, wherein the tip tapers to a point.

18. A predilator comprising:
   a shaft having a distal tip and an inner lumen, the distal tip tapering to and forming a point, the distal tip having helical threadings; and
   a rapid exchange element, the rapid exchange element being rotatably coupled to the shaft such that the shaft is rotatable with respect to the rapid exchange element and fixed from movement along a length of the shaft.

19. The predilator of claim 18, further comprising an aperture in the distal tip, the aperture offset from a central axis of the shaft.

20. The predilator of claim 19 wherein the distal tip comprises threadings located distal to the aperture.

21. The predilator of claim 18, further comprising a plurality of apertures in the distal tip in fluid communication with said inner lumen, the predilator configured to draw removed lesion material through said apertures and said inner lumen.

22. The predilator of claim 18, wherein a rotatable coupling between the rapid exchange element and the shaft comprises a raised flange and a recess, either the rapid exchange element or the shaft comprising the flange, the other comprising the recess, at least a portion of the raised flange oriented in the recess.

23. A device comprising:
   a catheter shaft defining a central axis, the shaft having a distal tip, the distal tip comprising a taper having helical threadings; and
   a rapid exchange element having a first internal passageway and a second internal passageway, a portion of the catheter shaft oriented in the first internal passageway, the rapid exchange element attached to the shaft by a rotatable coupling, said rotatable coupling comprising a raised flange and a recess, either the rapid exchange element or the shaft comprising the flange, the other comprising the recess, at least a portion of the raised flange oriented in the recess.

\* \* \* \* \*